United States Patent
Kirsh

(10) Patent No.: US 10,675,414 B2
(45) Date of Patent: Jun. 9, 2020

(54) SYRINGE FOR VISCOUS FLUIDS

(71) Applicant: Quark Distribution, Inc., New York, NY (US)

(72) Inventor: Ross Kirsh, New York, NY (US)

(73) Assignee: QUARK DISTRIBUTION, INC.

( * ) Notice: Subject to any disclaimer, the term of this patent is extended or adjusted under 35 U.S.C. 154(b) by 413 days.

(21) Appl. No.: 15/488,595

(22) Filed: Apr. 17, 2017

(65) Prior Publication Data
US 2018/0093044 A1 Apr. 5, 2018

Related U.S. Application Data

(60) Provisional application No. 62/324,580, filed on Apr. 19, 2016.

(51) Int. Cl.
*A61M 5/31* (2006.01)
*A61M 5/315* (2006.01)
*A61C 5/62* (2017.01)

(52) U.S. Cl.
CPC ...... *A61M 5/31586* (2013.01); *A61M 5/3129* (2013.01); *A61M 5/3148* (2013.01); *A61M 5/31511* (2013.01); *A61C 5/62* (2017.02)

(58) Field of Classification Search
CPC .......... A61M 5/31583; A61M 5/31586; A61M 5/3129; A61M 5/3148; A61M 5/31511; A61C 5/62
See application file for complete search history.

(56) References Cited

U.S. PATENT DOCUMENTS

| | | | | |
|---|---|---|---|---|
| 6,666,843 | B1 * | 12/2003 | Alexandre | A61M 5/30 604/68 |
| 6,712,794 | B2 * | 3/2004 | Kust | A61B 17/8822 604/211 |
| 6,899,699 | B2 * | 5/2005 | Enggaard | A61M 5/20 604/207 |
| 7,261,559 | B2 * | 8/2007 | Smith | A61C 5/62 433/89 |
| 7,811,263 | B2 * | 10/2010 | Burren | A61M 5/24 604/207 |
| 2003/0040701 | A1 * | 2/2003 | Dalmose | A61M 5/31596 604/87 |
| 2004/0260303 | A1 * | 12/2004 | Carrison | A61B 17/3472 606/92 |
| 2008/0033347 | A1 * | 2/2008 | D'rrigo | A61M 5/347 604/30 |
| 2009/0105685 | A1 * | 4/2009 | Stroem Hansen | A61M 5/30 604/500 |

(Continued)

*Primary Examiner* — Nathan R Price
*Assistant Examiner* — Courtney B Fredrickson
(74) *Attorney, Agent, or Firm* — Antonio Papageorgiou; Meister Seeling & Fein LLP

(57) ABSTRACT

A syringe is provided that includes a tubular body having a top end and a bottom end; a barrel portion having an orifice at a top end of the barrel portion for dispensing a fluid, the tubular body rotatably coupled to the top end of the tubular body; and a plunger body disposed within a bore of the barrel portion and within the tubular body, the plunger body includes a threaded portion that engages threads within the tubular body that cause the plunger body to move vertically within the bore of the barrel between a retracted position and a fully extended position with a twisting of the barrel portion.

21 Claims, 17 Drawing Sheets

(56) References Cited

U.S. PATENT DOCUMENTS

2010/0234799 A1* 9/2010 Paris ................. A61C 5/62
                                                        604/82
2014/0163478 A1* 6/2014 Hoppe ............... A61M 5/24
                                                        604/208

* cited by examiner

SYRINGE FOR VISCOUS FLUIDS

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND

The present application relates to syringes and more specifically syringes for dispensing viscous fluids.

A number of syringe designs have been used to dispense various liquids. However, prior designs are not well suited to dispensing certain viscous liquids, such as edible oils. Specifically, certain edible oils may thicken or solidify based on changes in environmental conditions, such as temperature and pressure, which negatively impact the ability of the syringe to dispense such oils, resulting in waste of the product being dispensed or at a minimum requiring additional effort to return the product to a usable form. Accordingly, there is a need for a syringe that overcomes or otherwise ameliorates the limitations of prior syringes.

SUMMARY OF THE INVENTION

In one aspect, a syringe is provided that includes a tubular body having a top end and a bottom end; a barrel portion having an orifice at a top end of the barrel portion for dispensing a fluid, the tubular body rotatably coupled to the top end of the tubular body; and a plunger body disposed within a bore of the barrel portion and within the tubular body, the plunger body includes a threaded portion that engages threads within the tubular body that cause the plunger body to move vertically within the bore of the barrel between a retracted position and a fully extended position with a twisting of the barrel portion.

In one embodiment, the tubular body includes an outer body and an inner body located within the inner body, the outer body includes at least one vertical slot within a hollow thereof, the inner body includes at least one vertical flange that fits into the at least one vertical slot to prevent rotational movement there between.

In one embodiment, the outer body includes at least one locking tab and the inner body includes at least one flange that engages the locking tab to prevent vertical movement between the inner and outer bodies once engaged.

In one embodiment, the plunger body includes a piston with a piston face having a shape and wherein the barrel portion has a head at the top end thereof, the head having a shape that compliments the shape of the piston face.

In one embodiment, the head and piston face are semi-spherical.

In one embodiment, the plunger body includes a plunger tip extending outward from the piston face, the orifice having a shape that compliments that of the plunger tip.

In one embodiment, the syringe includes a cap and wherein tubular body includes a threaded member for interlocking the cap to the tubular body.

In one embodiment, the syringe includes a cap that covers at least part of the barrel portion, the cap includes a plug extending outward therefrom into the orifice of the barrel portion.

In one embodiment, the plunger body includes a piston with a piston face having a plunger tip extending outward from the piston face into the orifice, when in a fully extended position the plunger tip interfering with the plug to prevent the cap from being installed.

In one embodiment, the syringe includes a threaded needle and wherein the barrel portion has a threaded collar at a top end thereof for attaching the threaded needle thereto.

In one embodiment, the plunger body includes a piston with an elastic gasket located circumferentially about the piston to form a seal between the piston and barrel portion.

In one embodiment, the gasket includes a plurality of piston rings extending outward from a piston skirt.

In one embodiment, the piston has a circumferential recess therein that accepts the gasket.

In one embodiment, the gasket forming an interference fit between it and the piston and the barrel bore.

In one embodiment, the barrel portion includes a circumferential groove at a bottom end thereof that engages a structure at a top end of the tubular body.

BRIEF DESCRIPTION OF THE DRAWINGS

The articles that are the subject of this application are illustrated in the figures of the accompanying drawings which are meant to be exemplary and not limiting, in which like references are intended to refer to like or corresponding parts, and in which.

DETAILED DESCRIPTION OF THE INVENTION

Subject matter will now be described more fully hereinafter with reference to the accompanying drawings, which form a part hereof, and which show, by way of illustration, exemplary embodiments in which the invention may be practiced. Subject matter may, however, be embodied in a variety of different forms and, therefore, covered or claimed subject matter is intended to be construed as not being limited to any example embodiments set forth herein; example embodiments are provided merely to be illustrative. It is to be understood that other embodiments may be utilized and structural changes may be made without departing from the scope of the present invention. Likewise, a reasonably broad scope for claimed or covered subject matter is intended. The following detailed description is, therefore, not intended to be taken in a limiting sense.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of exemplary embodiments in whole or in part.

Figure 1:
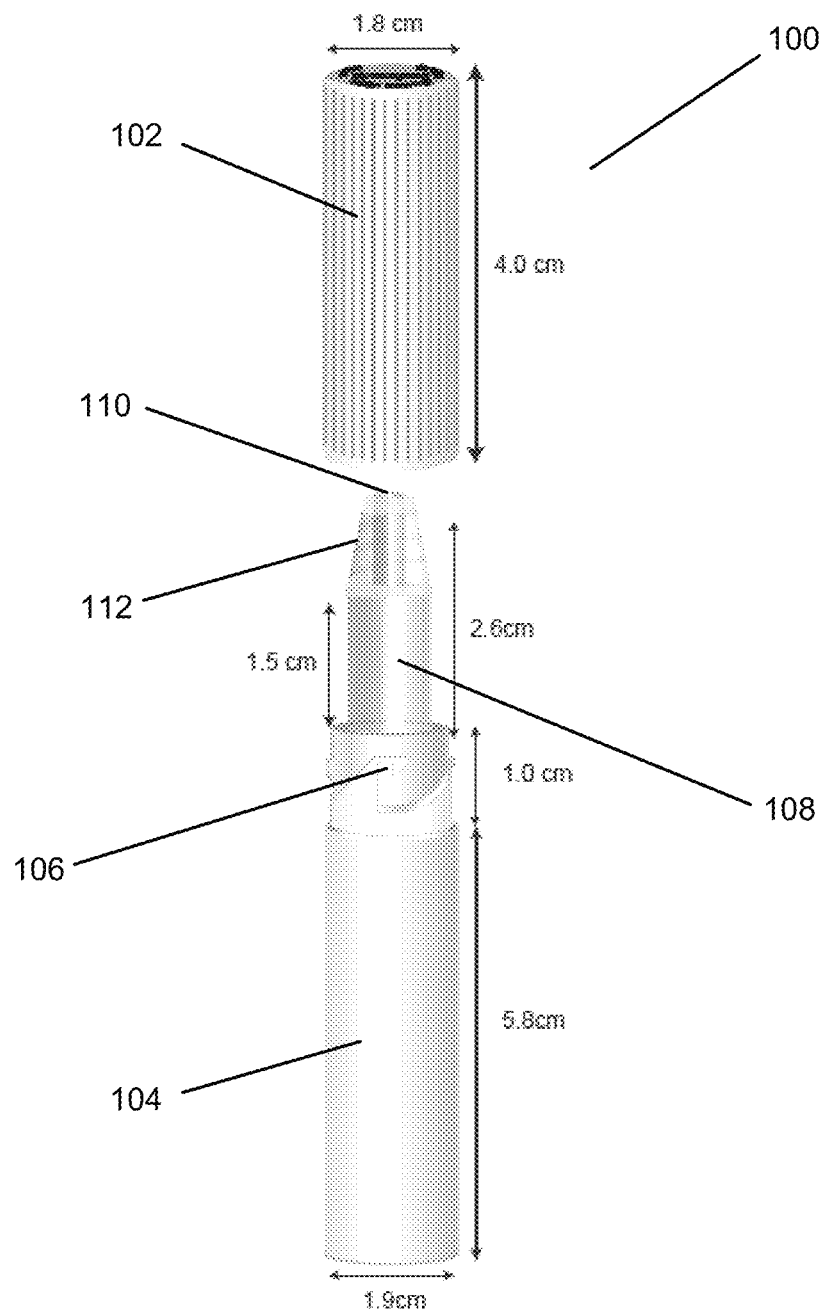
FIG. 1 illustrates a syringe according to one embodiment of the syringes disclosed herein.
Figures 3A, 3B:
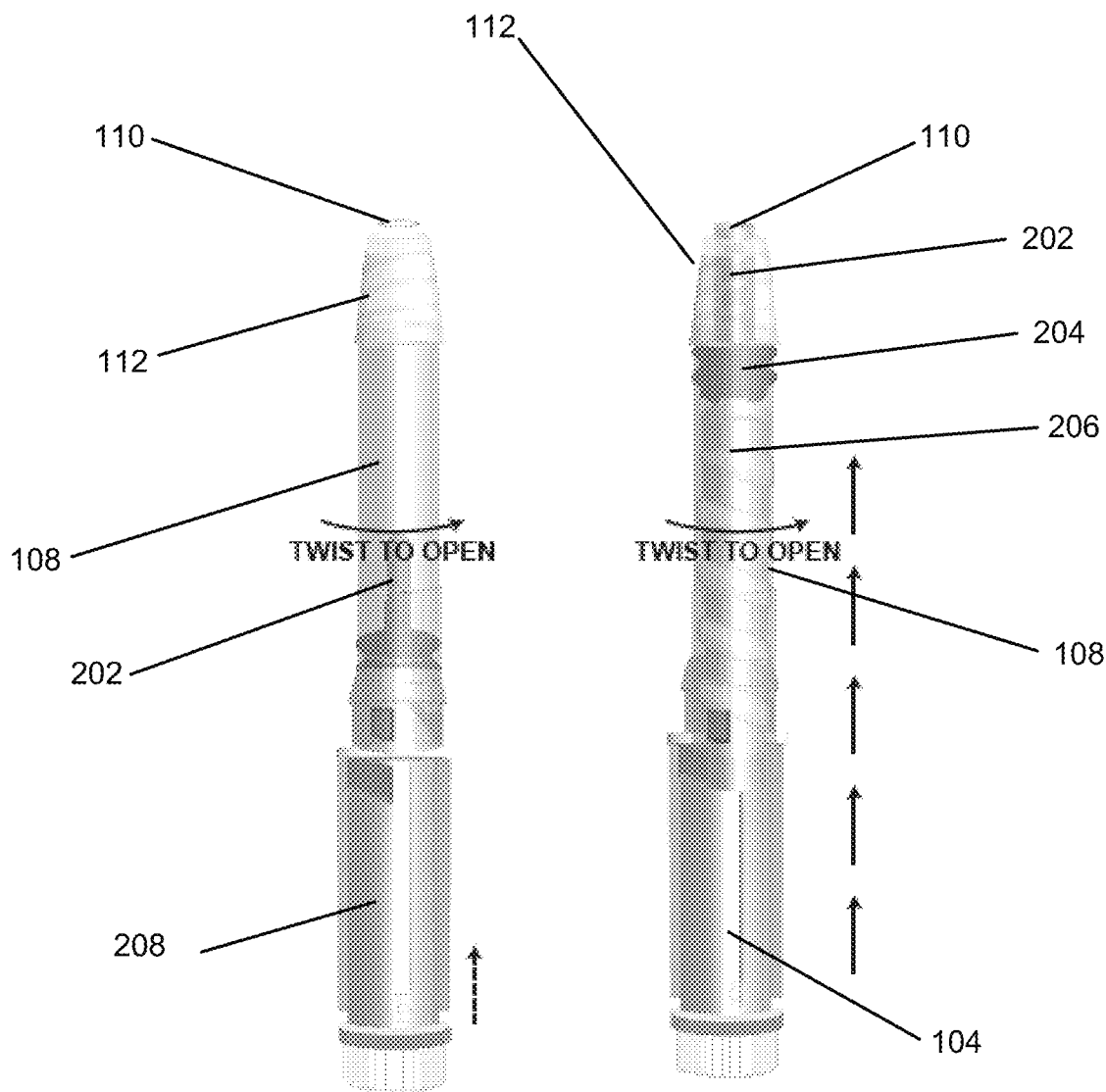
FIGS. 3A and 3B illustrate the operation of a syringe with a plunger according to one embodiment of the syringes disclosed herein.

FIG. 1 presents a syringe 100 for dispensing viscous fluids or more particularly liquids, such as edible oils or products containing edible oils, including olive, peanut, soybean, corn, or any other type of vegetable oil, as well as animal-based oils. Syringe 100 includes a cap 102 and a syringe assembly. The syringe assembly includes a syringe outer body 104 having a threaded member 106 at a top end of the body 104 for attaching the cap 102 to the syringe body 104. The syringe assembly further includes a sub-assembly having a barrel portion 108 with an orifice 110 at the top end of the barrel 108. The barrel portion 108 is preferably rotatably coupled to at least one of the body 104 and the sub-assembly (as shown in FIGS. 3A and 3B) at their respective bottom and top ends. Barrel 108 may also include a grip or friction portion (knurling) for ease of gripping and twisting barrel 108 by hand or fingers. The barrel portion 108 may further have collar 112 at the top end for attaching a needle thereto, as discussed in greater detail below.

Figure 2:
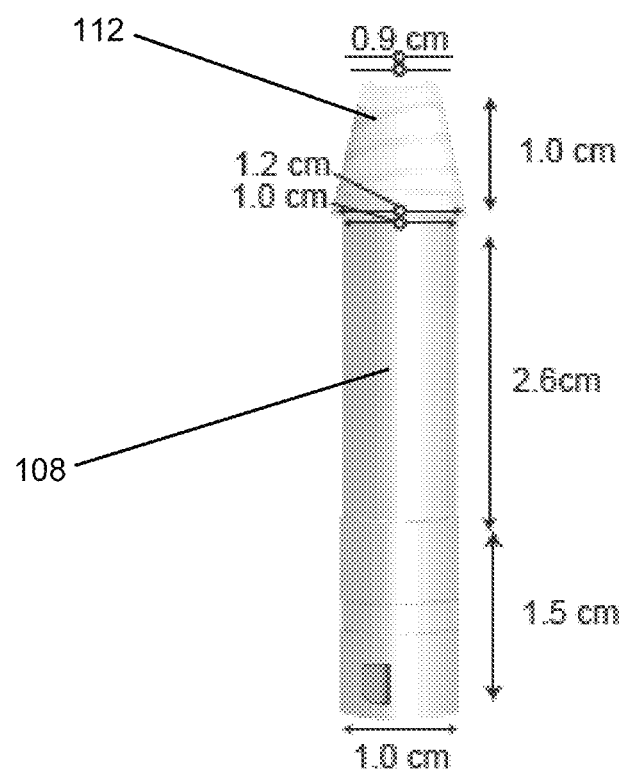
FIG. 2 illustrates a syringe barrel according to one embodiment of the syringes disclosed herein.

Cap 102 may be used to cover the barrel portion 108 of syringe 100 when not in use. The cap 102 may be removably secured to the body 104, for example, by twisting and interlocking the cap 102 to threaded member 106. Syringe body 104 may further include a cavity 804 at the bottom end of the body 104 for storing a tubular needle therein. In this regard, the needle may be removed from the cavity 804 and optionally removably attached to the collar 112, which is preferably threaded, for dispensing the viscous liquid contained in the barrel through orifice 110 and the tubular needle. FIG. 1 and FIG. 2 include exemplary dimensions for the components of syringe 100.

One or more components of syringe 100 may be constructed from plastic, rubber, glass, or any other suitable materials. Body 104 may further include a scroll wrapper that may be wrapped several times and adhered around body 104. The scroll wrapper may be peeled and unfurled to expose product information or directions within the scroll. The scroll wrapper may include an adhesive that allows the wrapper to be re-adhered to the body 104 in a furled state after unfurling.

FIGS. 3A and 3B present a syringe sub-assembly according to one embodiment of the present invention. The sub-assembly includes the barrel 108, an inner syringe body 208, and a plunger body 206. The tubular barrel 108 is rotatably connected to the inner body 208 at the top thereof, which body 208 preferably includes a threaded section therein. The plunger body 206 is disposed within the hollow of tubular barrel 108 and the hollow of the inner body 208, and is capable of moving vertically (from the top to the bottom of the syringe and reverse) within the hollow thereof anywhere in between a fully extended and retracted positions, as shown. Plunger body 206 preferably includes complementary threading that engages the threading within the inner body 208. In this regard, rotating or twisting the barrel 108 relative to the body 208 causes the plunger 108 to move vertically within the barrel 108. That is, turning barrel 108 either clockwise or counter-clockwise, in relation to syringe body 104/208, may cause piston 204 located at the top end of the plunger body 206 to be elevated or lowered, via plunger body 206, within barrel 108. Elevating piston 204 causes fluid that may be contained in barrel 108 to be dispensed out of orifice 110. Piston 204 may be constructed from plastic, rubber, or a combination of both.

Figure 4:
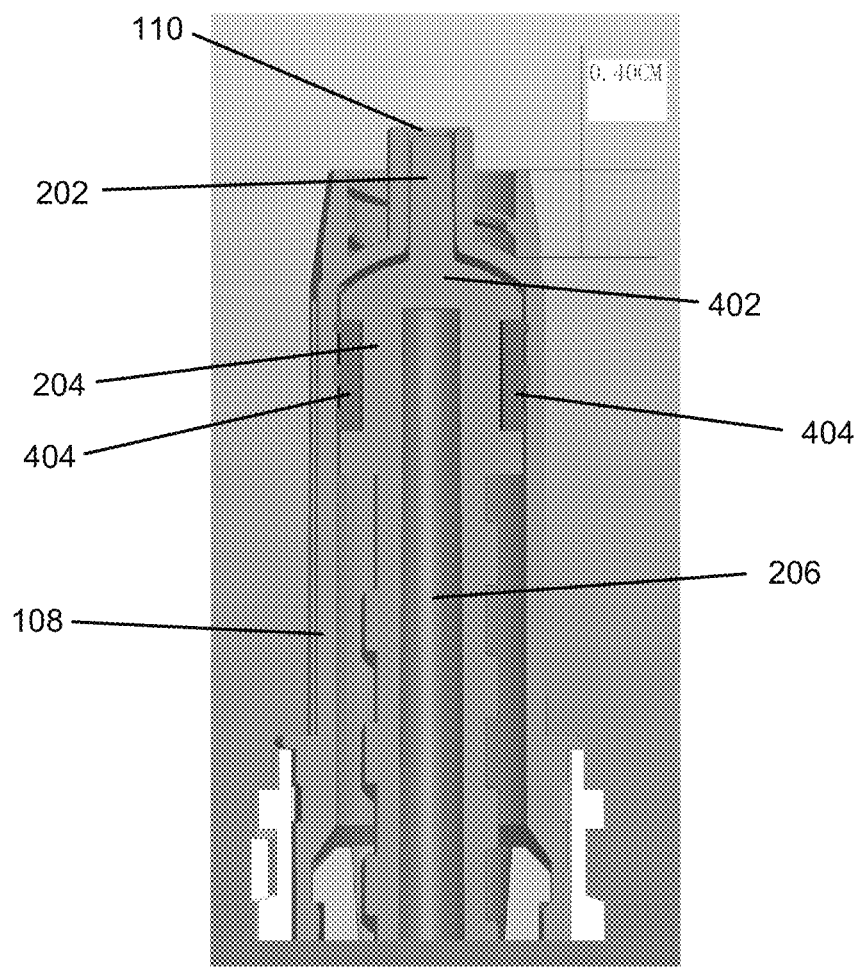
FIG. 4 illustrates a cross section of a syringe according to one embodiment of the syringes disclosed herein.
Figure 7:
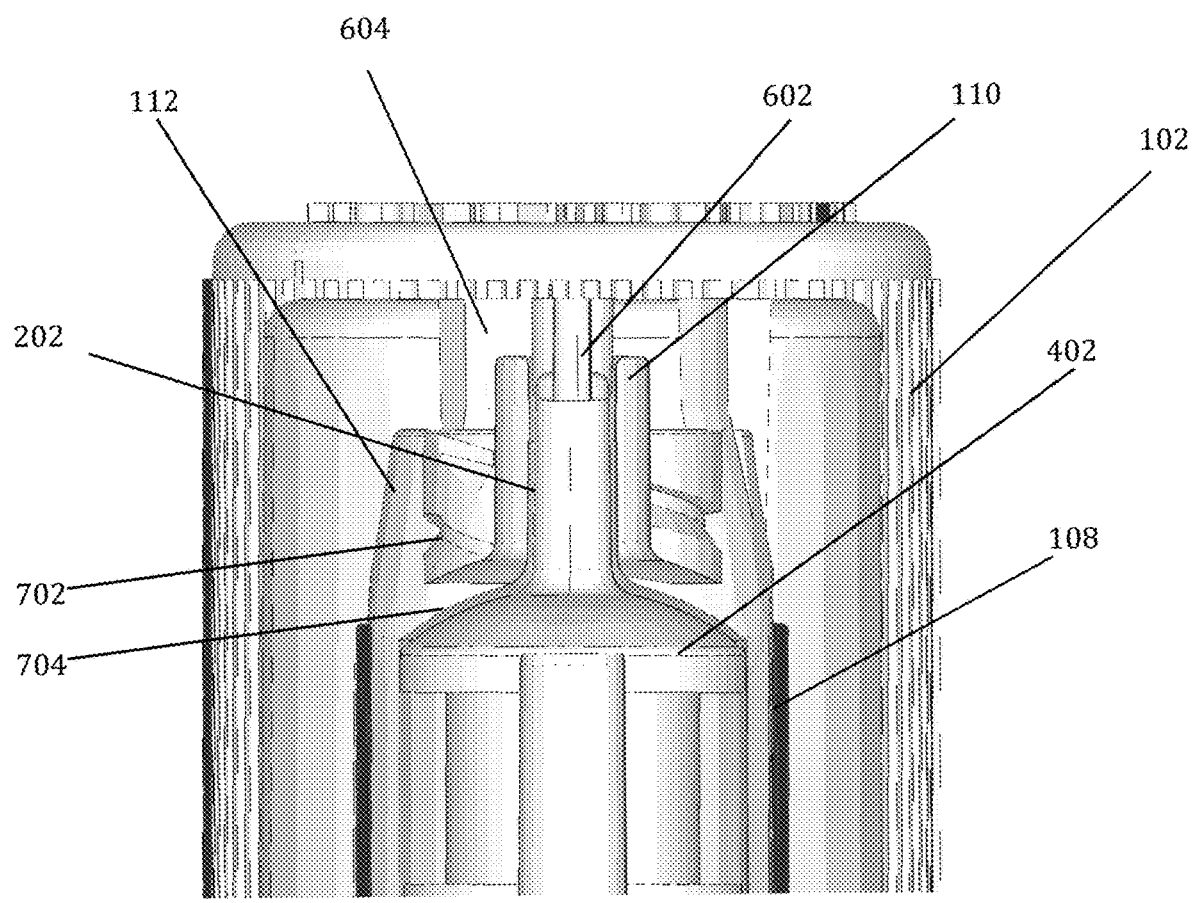
FIG. 7 illustrates a cross section of a syringe cap installed over a syringe assembly according to one embodiment of the syringes disclosed herein.

The piston 204 may include a tip 202 extending from the face of the piston 204. The tip 202 preferably has a shape that closely resembles or otherwise matches the shape of the orifice 110 so that the space between these components is minimized. In this regard, elevating of piston 204 may further cause plunger tip 202 to be inserted into and through orifice 110 to ensure that essentially all of the content within barrel 108 is dispensed from the barrel 108 and orifice 110, as shown in FIG. 4. Cap 102 may further include a plug that extends into the opening of orifice 110 when the cap 102 is in place over the syringe 100, as shown in FIG. 7. In this instance, the plunger tip 202 may extend into the orifice sufficient to interfere with the plug in the cap 102 when the plunger is in the fully extended position, thereby prohibiting cap 102 from being secured onto the top portion of syringe 100 at that position.

FIG. 4 presents a cross section of the plunger body located within the barrel 108. In the illustrated embodiment, piston 204 is fully elevated to form a complementary fit with the top of barrel 108 and plunger tip 202 is inserted through orifice 110. Piston 204 includes a semi-circular or semi-spherical top surface (face) from which the plunger tip 202 extends, with a complimentary shape in the top of the barrel 108 (head) to ensure that essentially the entirety of the liquid contained in barrel 108 is dispensed therefrom, regardless of the consistency of the liquid. Piston 204 may also include rubber gaskets 404 that surrounds piston 204 to form a tight seal between the piston 204 and barrel 108. According to another embodiment, the entirety of piston 204 may be made of rubber or any other suitable material. The gasket 404 preferably includes a plurality of piston rings that extend circumferentially around the piston 204 and out from the piston skirt to prevent any flow past the rings that may results because of pressure built up during extension of the piston 204.

Figure 5:
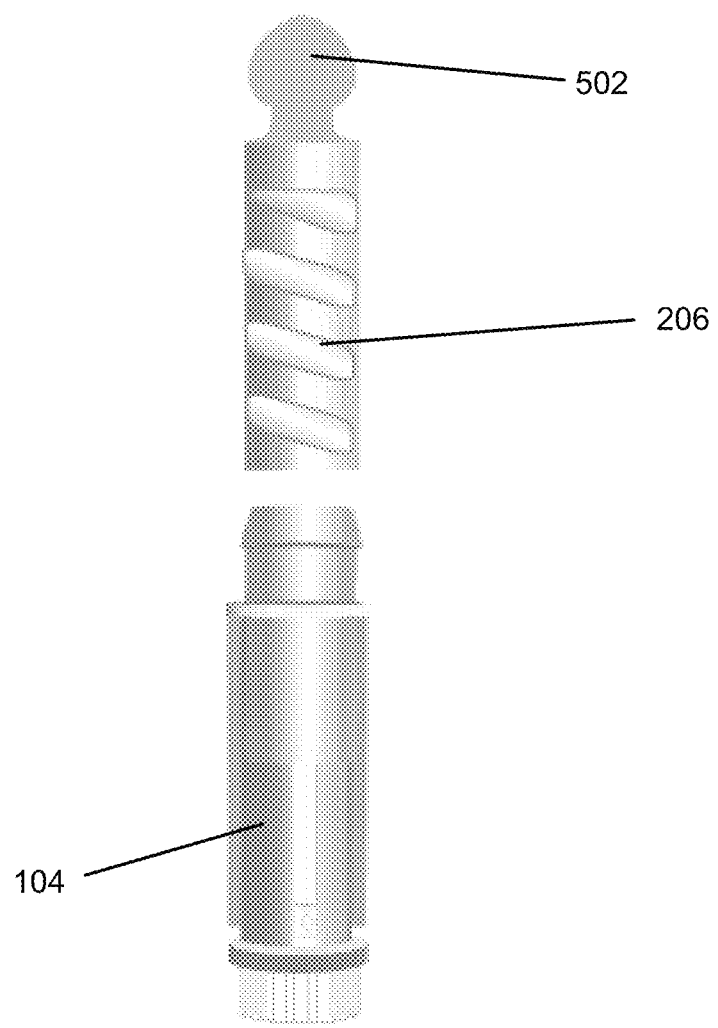
FIG. 5 illustrates a plunger body according to one embodiment of the syringes disclosed herein.

FIG. 5 presents a plunger body according to another embodiment. Piston 502 may include a spade-like or heart-like shape to form a complementary fit with a top of barrel 108.

Figure 6:
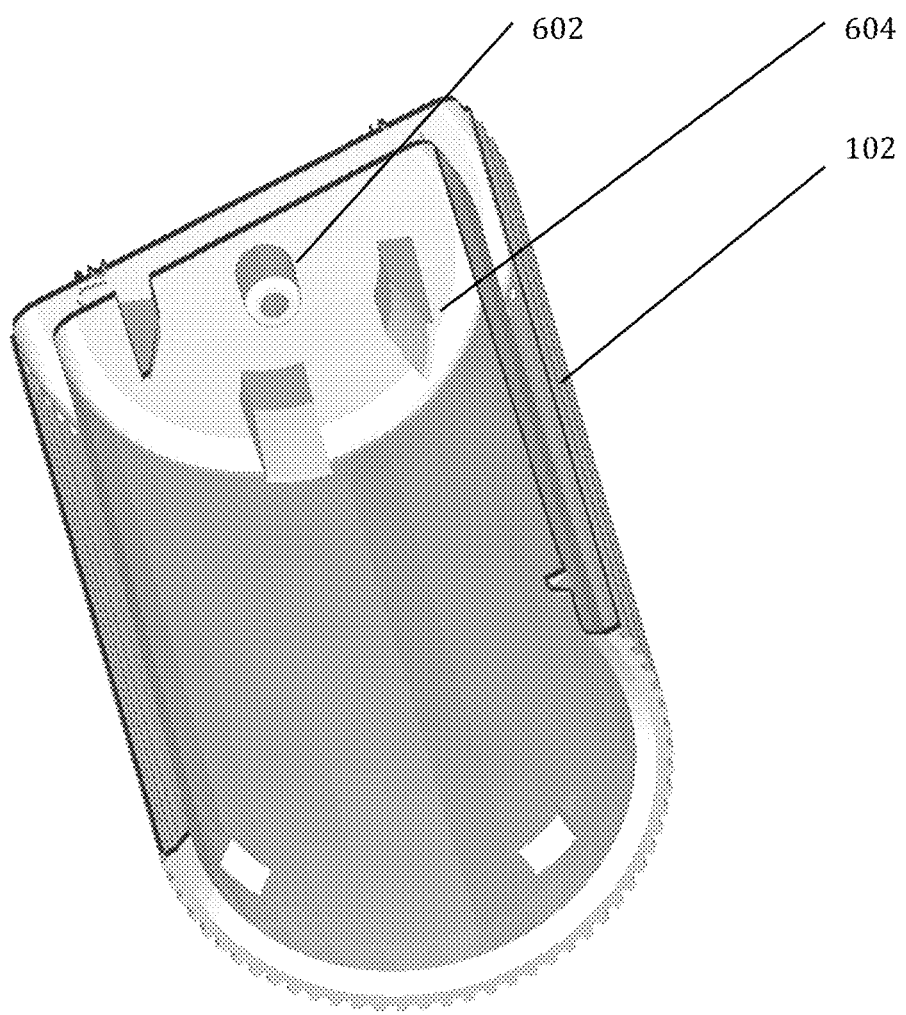
FIG. 6 illustrates a cross section of a syringe cap according to one embodiment of the syringes disclosed herein.

FIG. 6 illustrates a cross section of an embodiment of a cap 102. In this instance, the cap 102 has a generally tubular structure with an opening at one end for receiving the barrel 108. At the opposite end of the opening is a top inner surface with a plug 602 extending therefrom. The plug 602 is located in the cap 102 so as to fit within the orifice 110 when placed over the barrel 108, as shown in FIG. 7. The cap 102 may further include a plurality of ramped members 604 that extend outward essentially orthogonally from the inner surface and circumferentially spaced around the plug 602. These members have ramped surfaces that face inwardly to stabilize the cap with regard to the collar 112 when installed on the syringe, as also shown in FIG. 7. That is, the angle of the ramped surfaces may correspond to the angle of the outwardly facing surfaces of the collar 112, as also shown in FIG. 7.

FIG. 7 illustrates a cross sectional view of the cap 102 installed over the near fully extended piston 402. In this embodiment, the elevation of the plug 602 is lower than the elevation of the top of the orifice 110 so that the plug 602 is at least partially disposed within the orifice 110. The orifice 110 generally has a tubular shape with a circular cross section having an inner diameter that is essentially equal to the diameter of the plug 602. Moreover, the shape of the plunger tip 202 is essentially cylindrical (optionally with a slight taper toward the top) and matches the shape of the inner surface of the orifice 110. The elevation at the top of the plunger tip 201 at the fully extended position is greater than the elevation of the plug 602 to prevent the cap 202 from being installed onto a fully extended piston 402. In this embodiment, the domed head 704 of the barrel 108 matches the domed piston 402 to minimize space between these components. Finally, the collar 112 has a tapered cylindrical shape with internal threading 702 for installing, for example, a needle thereon.

Figure 8:
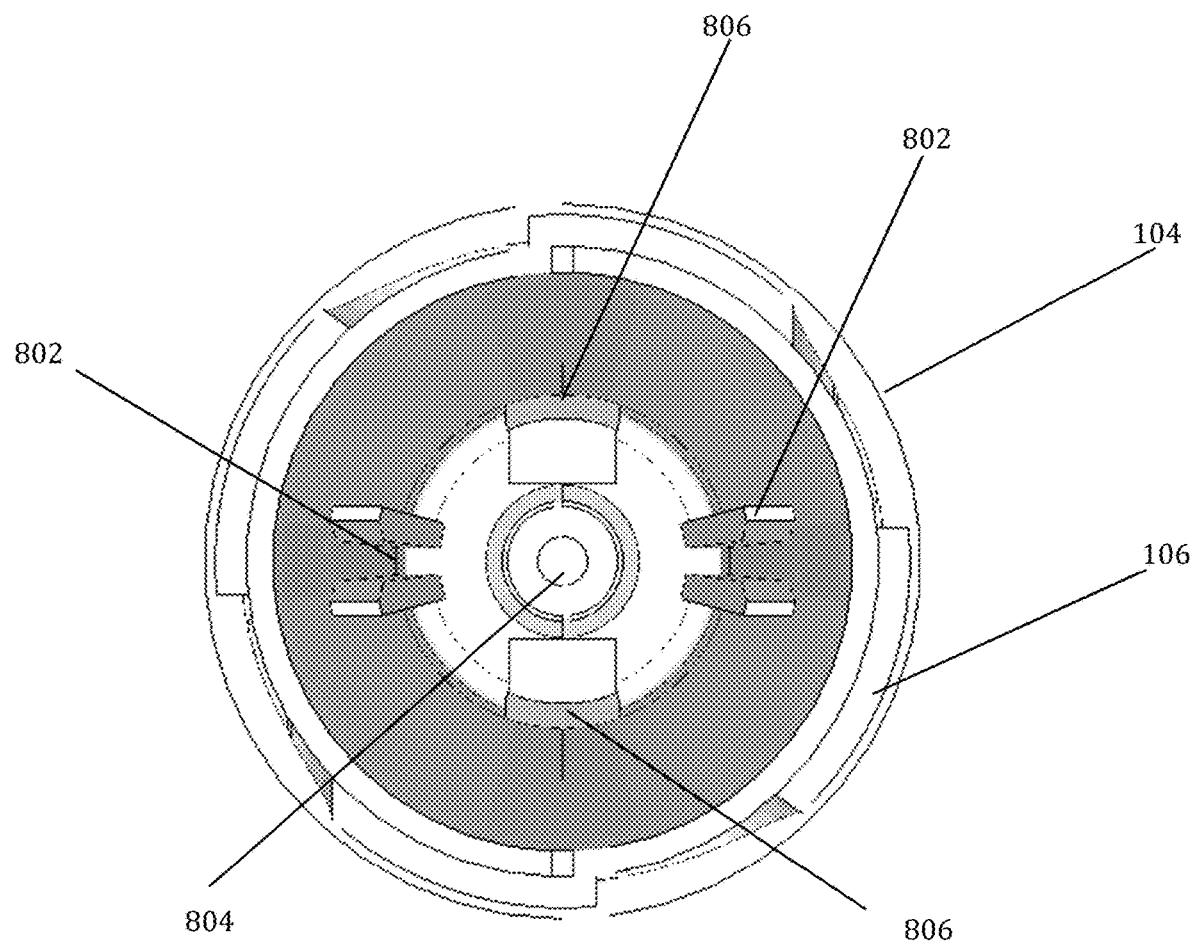
FIG. 8 illustrates a top view of an outer body of a syringe assembly according to one embodiment of the syringes disclosed herein.

FIG. 8 illustrates a top view of an outer body 104 of a syringe assembly according to one embodiment of the syringes disclosed herein. The body 104 has a generally tubular shape with one or more vertical/lengthwise slots 802 therein. Slots 802 generally accept corresponding lengthwise flanges on the syringe subassembly, as discussed in greater detail below. Body 104 may further include an aperture for accepting a needle and one or more locking tabs 806 for locking the sub-assembly vertically within the body 104, as also discussed in greater detail below.

Figure 9:
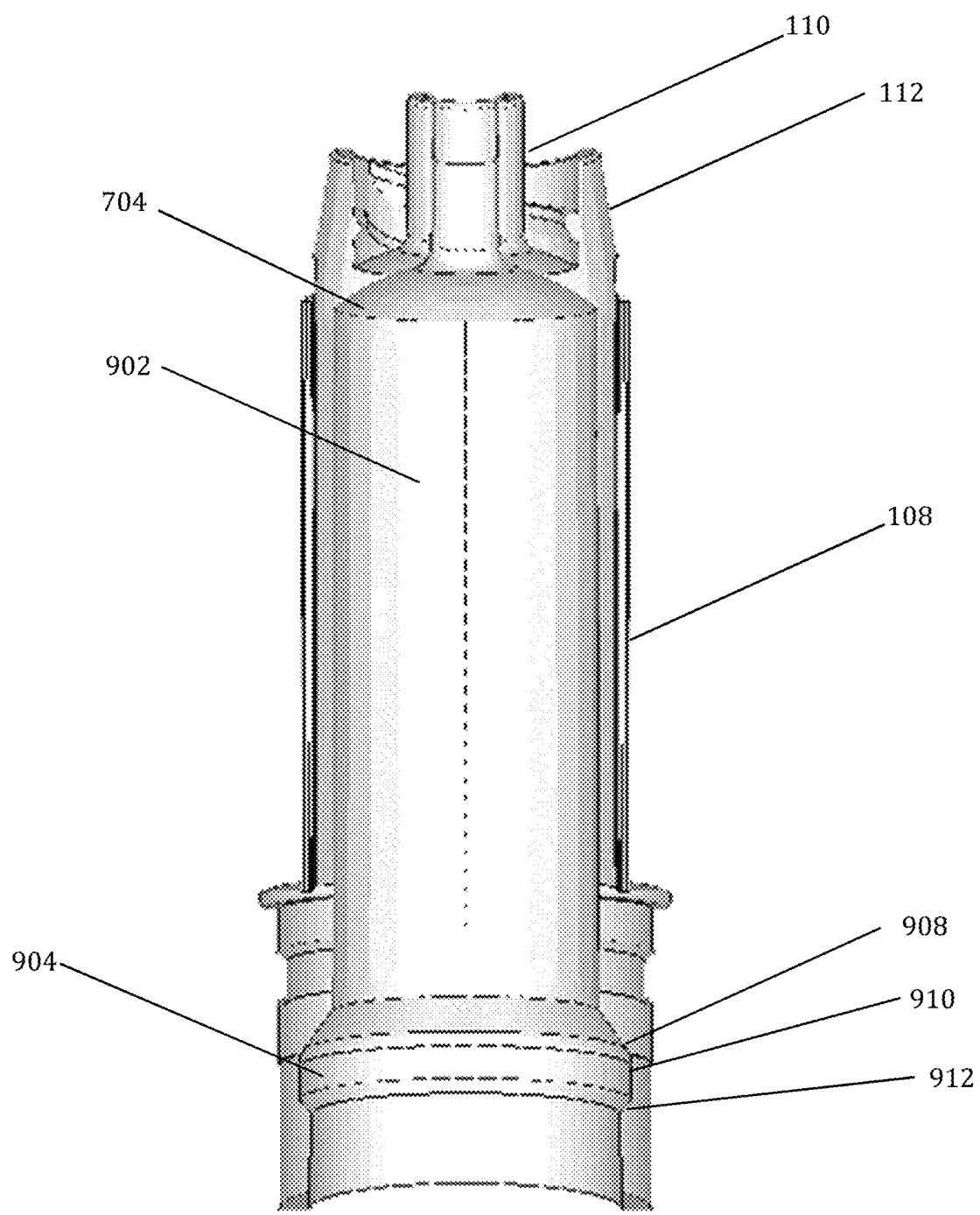
FIG. 9 illustrates a cross section of a barrel portion of a syringe assembly according to one embodiment of the syringes disclosed herein.
Figure 17:
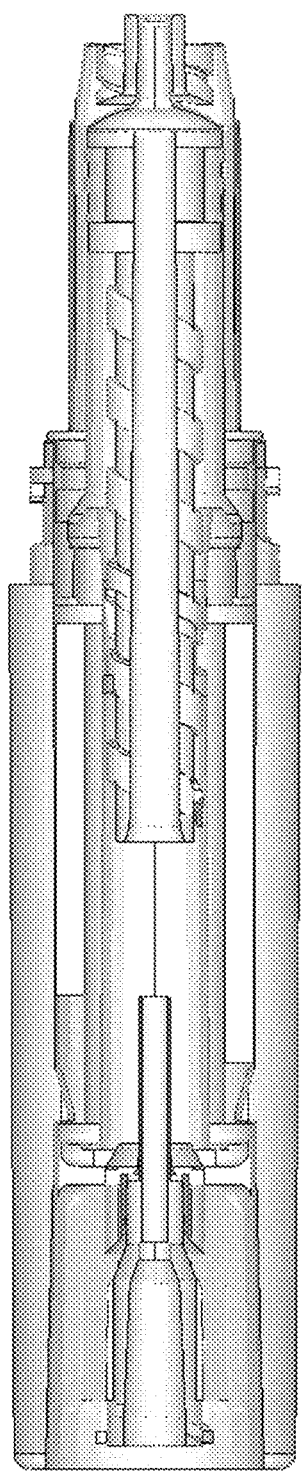

FIG. 9 illustrates a cross section of an embodiment of a barrel portion 108. The barrel 108 has a bore 902 with a mechanism for rotatably fastening the barrel 108 to the syringe sub-assembly or, more particularly, the inner body 208. That is, the barrel 108 is arrested against vertical movement relative to the sub-assembly, while allowing the barrel 108 to rotate about the axis thereof with a twisting motion by the user. In one embodiment, this mechanism comprises a circumferential groove 904 in the walls of the bore 902 that engage a corresponding structure on the sub-assembly or inner body 208. The circumferential groove 904 may be defined with first and second inwardly inclined walls 908, 912 separated by a recessed wall 910. In this instance, the inward incline of walls 908 and 912 maintain the level of the recessed wall 910 below that of the bore 902 to accommodate the structure on the inner body 208, as shown in FIG. 17.

Figure 10:
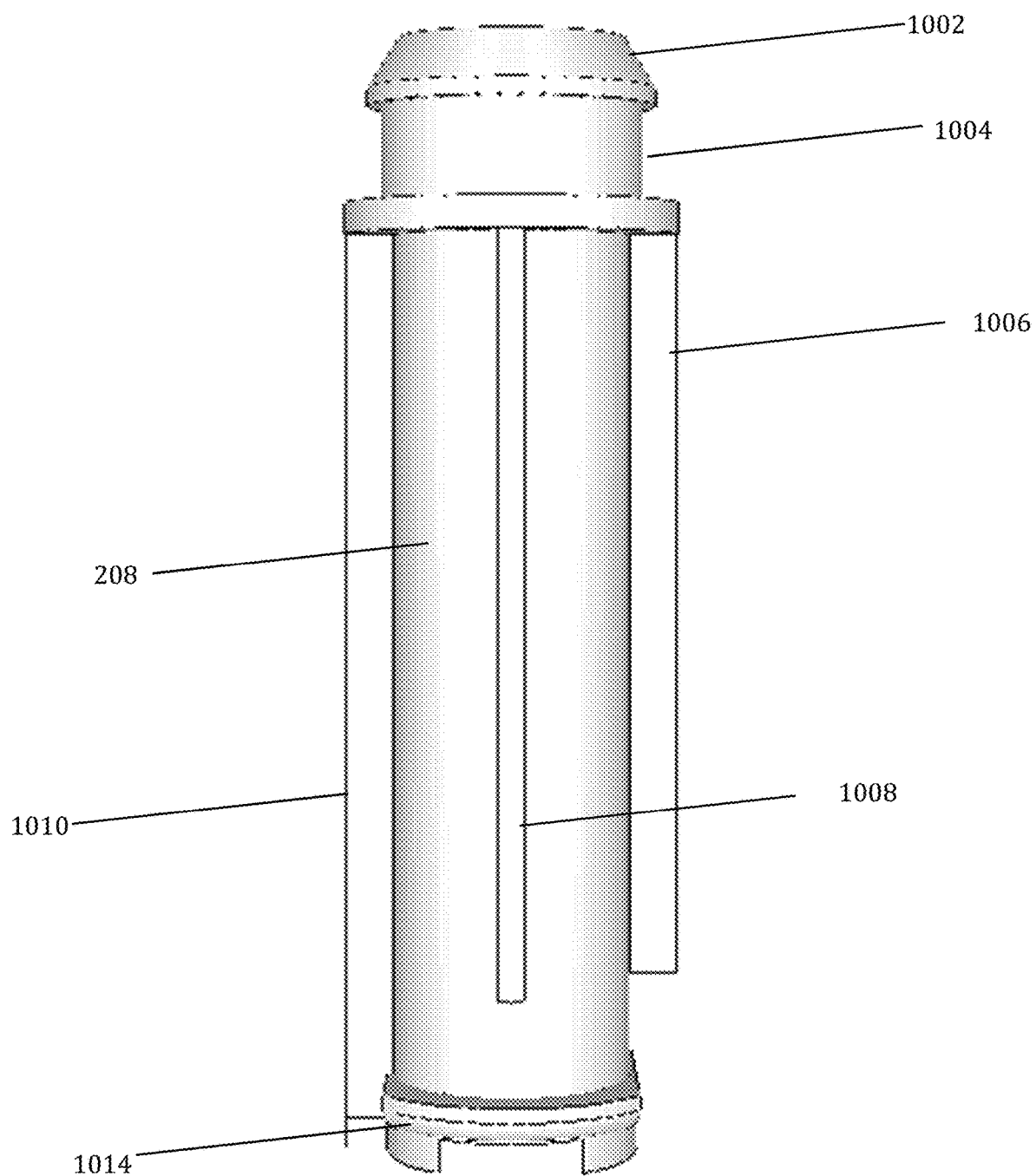
FIGS. 10-11 illustrate front and side views an inner body of a syringe assembly according to one embodiment of the syringes disclosed herein.
Figure 11:
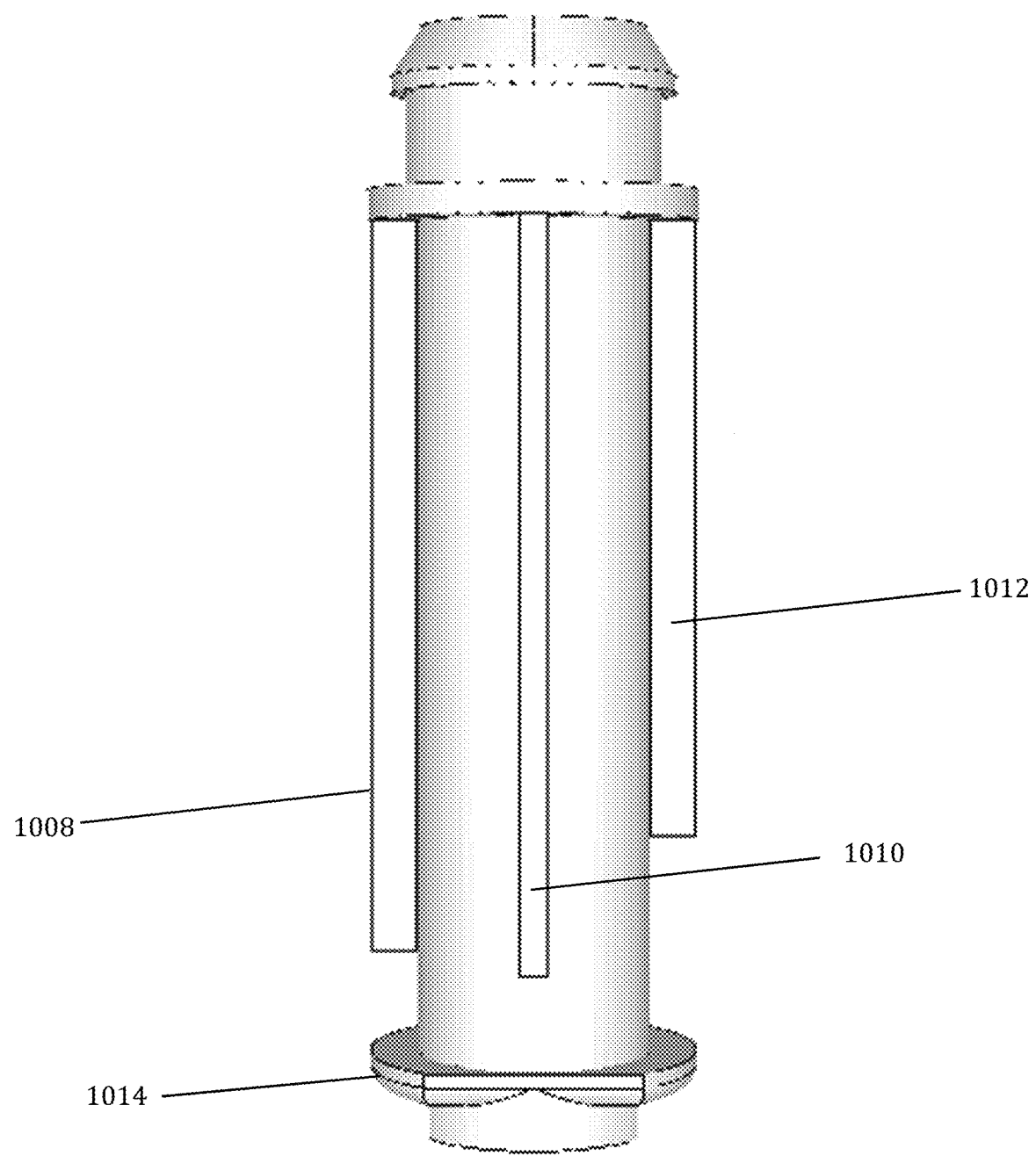

FIGS. 10-11 illustrate front and side views of an embodiment of an inner body 208. Inner body 208 includes a structure that engages the recess in groove 904 of the barrel 108. This structure includes a vertical section 1004 topped with a tapered protrusion 1002. The inner body 208 also includes at least one vertical flange 1006, 1008, 1010, 1012 that are inserted into the vertical slots 802 of the outer body 104 to prevent rotational movement there between. The Inner body 208 may also include a flange 2014 that engages the locking tabs 806 in the outer body 104 to prevent vertical movement between the inner and outer bodies once engaged.

Figure 12:
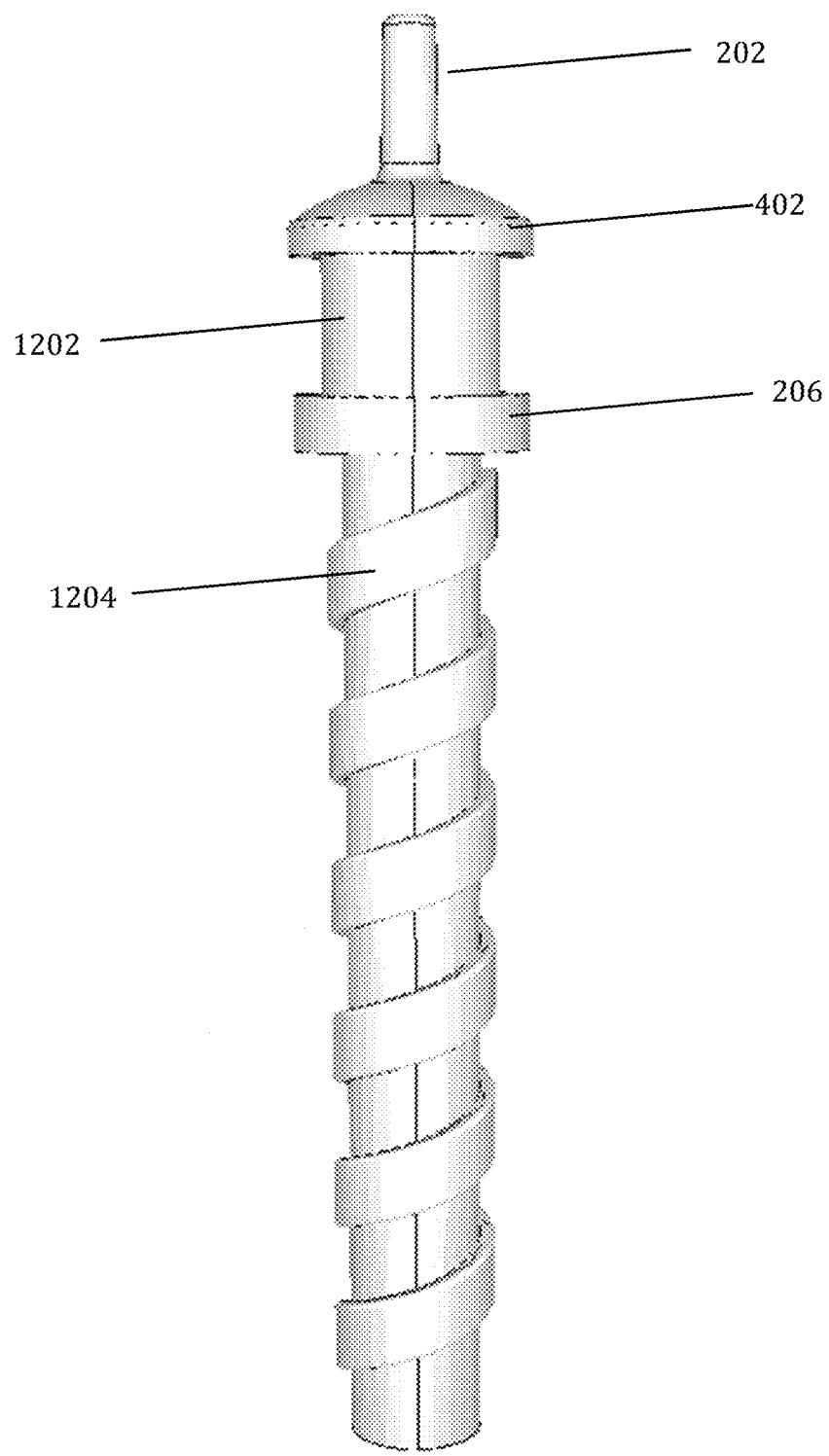
FIG. 12 illustrates a plunger body of a syringe assembly according to one embodiment of the syringes disclosed herein.
Figure 13:
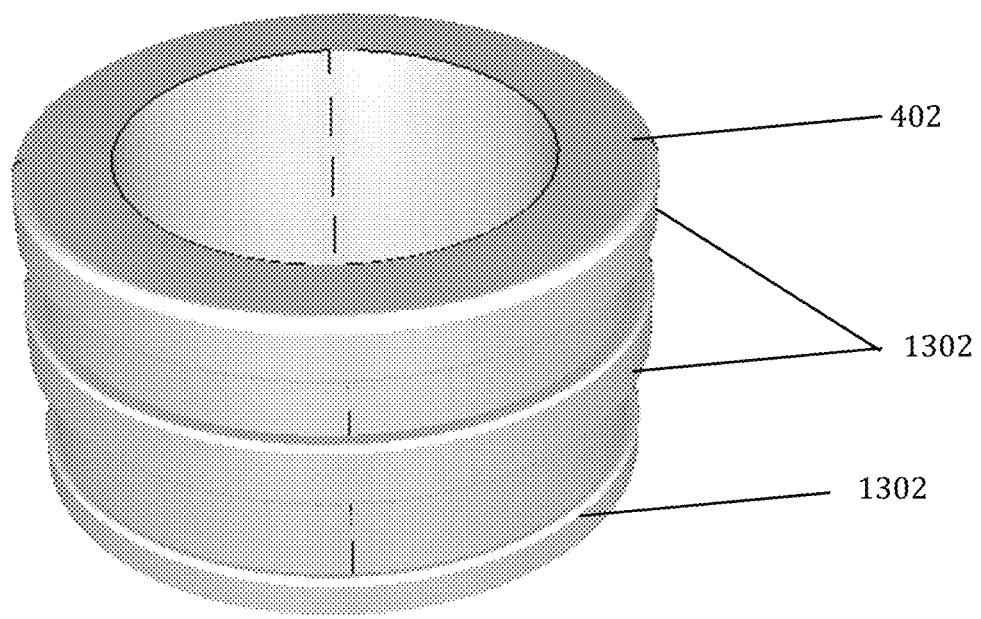
FIG. 13 illustrates a gasket for use with a syringe assembly according to one embodiment of the syringes disclosed herein.
Figure 15:
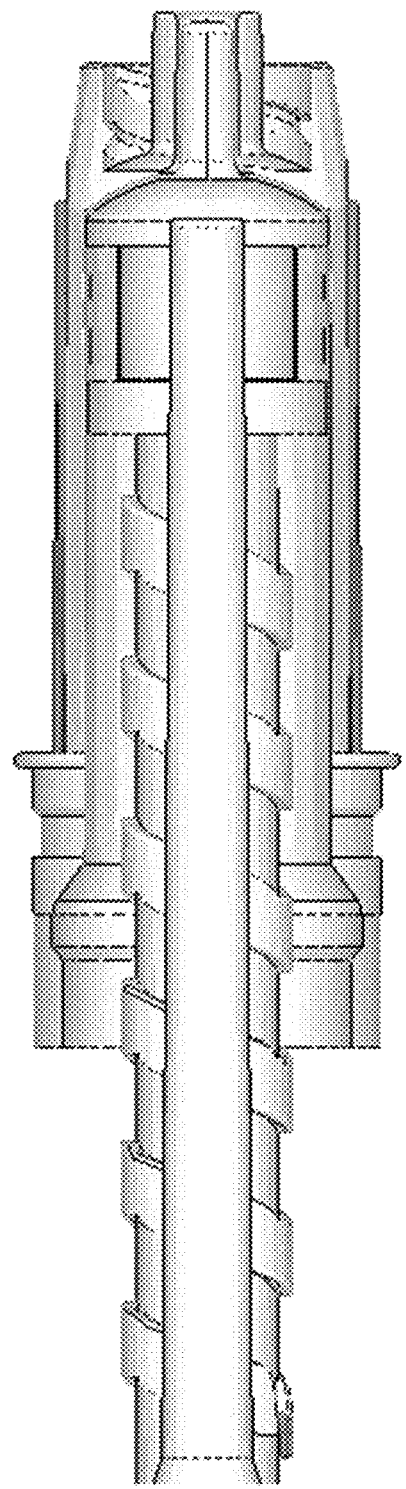
FIGS. 15-17 illustrate cross sections of a syringe assembly according to one embodiment of the syringes disclosed herein.
Figure 16:
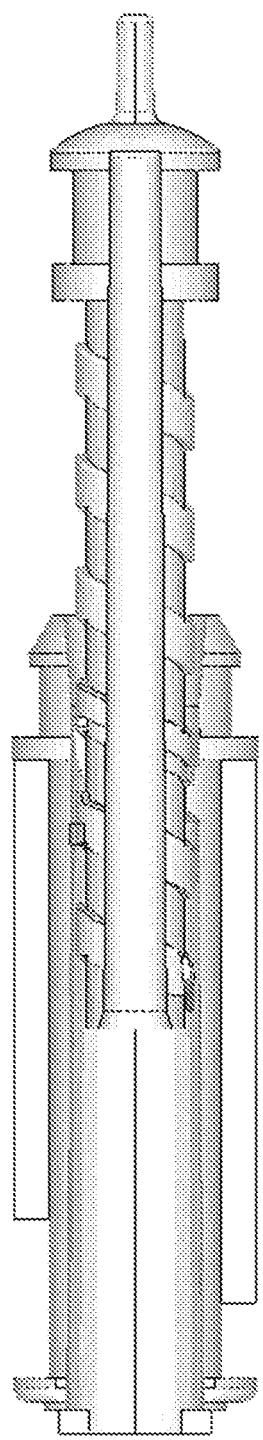

FIG. 12 illustrates a plunger body 206 according to one embodiment. The plunger body 206 includes a piston 402 at a top end thereof with a tip 202 extending therefrom. The body 206 includes a threaded portion 1204 extending between the piston and bottom end of the plunger body 206. This threaded portion 1204 engages a corresponding threaded portion within the inner body 208 to cause the piston 402 to move vertically (up and down) within the bore of the barrel 108 with a twisting motion of the barrel 108 relative to the inner body 208, as shown in FIG. 16. The plunger body may further include a circumferential recess 1202 in the piston skirt that accepts a tubular gasket 404, such as the gasket shown in FIG. 13. The gasket 404 preferably includes a plurality of piston rings molded thereon 1302. The gasket 404 is preferably made of an elastic material, such as a rubber material, that conforms to the bore 902 of the barrel 108. The thickness of the gasket 404 is preferably such that an interference fit between it and the piston 402 and bore 902 is maintained, as shown in FIG. 15. This interference fit serves two purposes: first, to resist any liquid in the barrel 108 from passing the piston/rings, and second, to maintain sufficient friction so that rotating the barrel 108 causes the plunger body 206 to rotate resulting in vertical movement of the piston 402 within bore 902.

Figure 14:
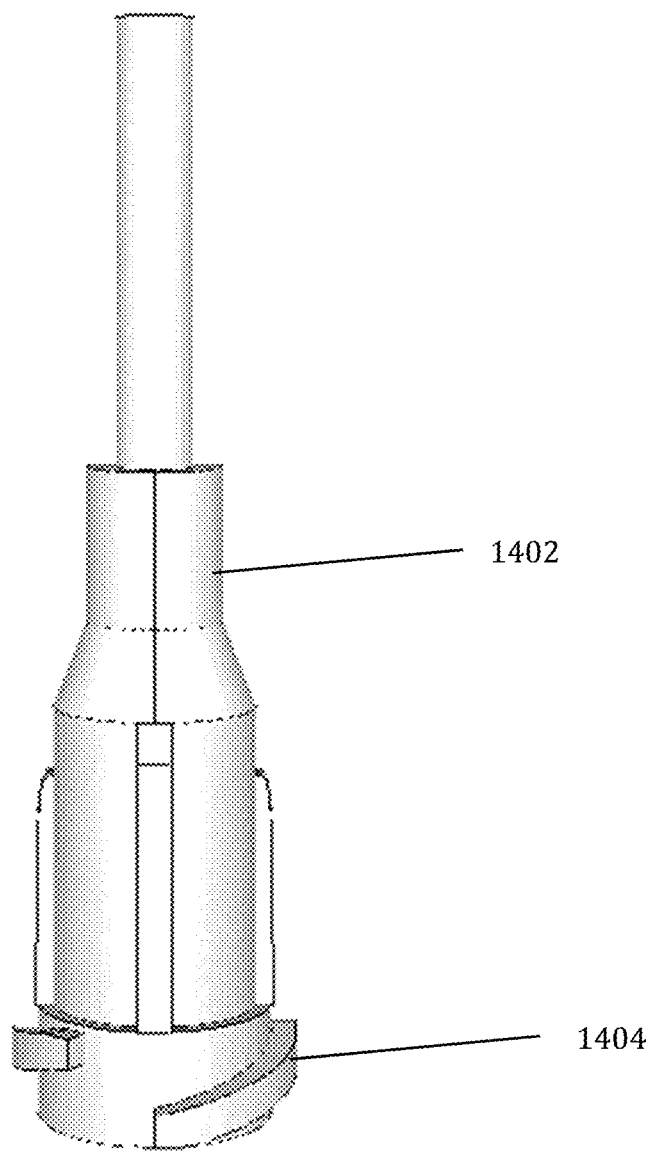
FIG. 14 illustrates a needle for use with a syringe assembly according to one embodiment of the syringes disclosed herein.

Referring to FIG. 14, a tubular needle 1402 according to one embodiment is shown. The tubular needle 1402 includes a threaded portion 1404 for the removable attachment thereof to the corresponding threading 702 of the collar 112 of the barrel 108. As indicated herein, the needle fits within the bottom end of the outer body 104, as shown in FIG. 17.

FIGS. 1 through 17 are conceptual illustrations allowing for an explanation of the present invention. Notably, the figures and examples above are not meant to limit the scope of the present invention to a single embodiment, as other embodiments are possible by way of interchange of some or all of the described or illustrated elements. Moreover, where certain elements of the present invention can be partially or fully implemented using known components, only those portions of such known components that are necessary for an understanding of the present invention are described, and detailed descriptions of other portions of such known components are omitted so as not to obscure the invention. In the present specification, an embodiment showing a singular component should not necessarily be limited to other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

The foregoing description of the specific embodiments will so fully reveal the general nature of the invention that others can, by applying knowledge within the skill of the relevant art(s) (including the contents of the documents cited and incorporated by reference herein), readily modify and/or adapt for various applications such specific embodiments, without undue experimentation, without departing from the general concept of the present invention. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

The invention claimed is:

1. A syringe comprising:
a tubular body having a top end and a bottom end;
a barrel portion having an orifice at a top end of the barrel portion for dispensing a fluid, the barrel portion rotatably coupled to the top end of the tubular body; and
a plunger body disposed within a bore of the barrel portion and within the tubular body, the plunger body comprising a threaded portion that engages threads within the tubular body that cause the plunger body to move vertically within the bore of the barrel between a retracted position and a fully extended position with a twisting of the barrel portion,
wherein the tubular body comprises an outer body and an inner body located within the outer body, the outer body comprising at least one vertical slot within a hollow thereof, the inner body comprising at least one vertical flange that fits into the at least one vertical slot to prevent rotational movement there between, and
wherein the outer body comprises at least one locking tab and the inner body comprises at least one flange that engages the locking tab to prevent vertical movement between the inner and outer bodies once engaged.

2. The syringe of claim 1, wherein the plunger body comprises a piston with a piston face having a shape and wherein the barrel portion has a head at the top end thereof, the head having a shape that compliments the shape of the piston face.

3. The syringe of claim 2, wherein the head and piston face are semi-spherical.

4. The syringe of claim 2, wherein the plunger body comprises a plunger tip extending outward from the piston face, the orifice having a shape that compliments that of the plunger tip.

5. The syringe of claim 1, comprising a cap and wherein tubular body comprises a threaded member for interlocking the cap to the tubular body.

6. The syringe of claim 1, comprising a cap that covers at least part of the barrel portion, the cap comprising a plug extending outward therefrom into the orifice of the barrel portion.

7. The syringe of claim 6, wherein the plunger body comprises a piston with a piston face having a plunger tip extending outward from the piston face into the orifice, when in a fully extended position the plunger tip interfering with the plug to prevent the cap from being installed.

8. The syringe of claim 1, comprising a threaded needle and wherein the barrel portion has a threaded collar at the top end thereof for attaching the threaded needle thereto.

9. The syringe of claim 1, wherein the plunger body comprises a piston with an elastic gasket located circumferentially about the piston to form a seal between the piston and barrel portion.

10. The syringe of claim 9, wherein the gasket comprises a plurality of piston rings extending outward from a piston skirt.

11. The syringe of claim 9, wherein the piston has a circumferential recess therein that accepts the gasket.

12. The syringe of claim 9, the gasket forming an interference fit between the gasket and the piston and the barrel bore.

13. The syringe of claim 1, wherein the barrel portion comprises a circumferential groove at a bottom end thereof that engages a structure at the top end of the tubular body.

14. A syringe comprising:
a tubular body having a top end and a bottom end;
a barrel portion having a head with a shape and an orifice at a top end of the barrel portion for dispensing a fluid therein, the barrel portion rotatably coupled to the top end of the tubular body; and
a plunger body disposed within a bore of the barrel portion and within the tubular body, the plunger body comprising:
a threaded portion that engages threads within the tubular body that cause the plunger body to move vertically within the bore of the barrel between a retracted position and a fully extended position with a twisting of the barrel portion,
a piston at a top end of the plunger body having a piston face having a shape that compliments the shape of that of the head, and
a plunger tip extending outward from the piston face, the orifice having a shape that compliments that of the plunger tip,
wherein the tubular body comprises an outer body and an inner body located within the outer body, the outer body comprising at least one vertical slot within a hollow thereof, the inner body comprising at least one vertical flange that fits into the at least one vertical slot to prevent rotational movement there between, and
wherein the outer body comprises at least one locking tab and the inner body comprises at least one flange that engages the locking tab to prevent vertical movement between the inner and outer bodies once engaged.

15. The syringe of claim 14, wherein the head and piston face are semi-spherical.

16. The syringe of claim 14, comprising a cap that covers at least part of the barrel portion, the cap comprising a plug extending outward therefrom into the orifice of the barrel portion.

17. The syringe of claim 16, wherein, when in a fully extended position, the plunger tip interferes with the plug to prevent the cap from being installed.

18. The syringe of claim 14, comprising a threaded needle and wherein the barrel portion has a threaded collar at the top end thereof for attaching the threaded needle thereto.

19. The syringe of claim 14, wherein the piston comprises an elastic gasket located circumferentially about the piston to form a seal between the piston and barrel portion.

20. The syringe of claim 19, wherein the gasket comprises a plurality of piston rings extending outward from a piston skirt.

21. The syringe of claim 19, the gasket forming an interference fit between the gasket and the piston and barrel bore.

* * * * *